United States Patent [19]

Comarmond et al.

[11] Patent Number: 4,812,467

[45] Date of Patent: Mar. 14, 1989

[54] N-(IMIDAZOLYLMETHYL)DI-PHENYLAZOMETHINES AND COMPOSITIONS CONTAINING THEM

[75] Inventors: Jacques Comarmond, Paris; Thomas Purcell, Montfort l'Amaury; Lydia Zard, Gif s/Yvette, all of France

[73] Assignee: Synthelabo, France

[21] Appl. No.: 66,531

[22] Filed: Jun. 26, 1987

[30] Foreign Application Priority Data

Jun. 27, 1986 [FR] France ............... 86 09331

[51] Int. Cl.[4] ............... A61K 31/415; C07D 233/64
[52] U.S. Cl. ............... 514/341; 514/400; 546/278; 548/342
[58] Field of Search ............... 548/342; 546/278; 514/314, 400; 564/316, 501

[56] References Cited

U.S. PATENT DOCUMENTS 4,558,062 12/1985 Kaplan ............... 548/342

FOREIGN PATENT DOCUMENTS 0133061 2/1985 European Pat. Off. ............ 548/342
2548183 1/1985 France ............... 548/342

OTHER PUBLICATIONS

Lowry et al., *An Intro. to Organic Chemistry,* 1951, p. 217.
Topliss, *J. of Medicinal Chemistry,* vol 15, No. 10, pp. 1006–1010, 1972.

*Primary Examiner*—Mary C. Lee
*Assistant Examiner*—Z. Northington
*Attorney, Agent, or Firm*—Wegner & Bretschneider

[57] ABSTRACT

A compound which is an N-(imidazolymethyl) diphenylazomethine derivative of the general formula (I)

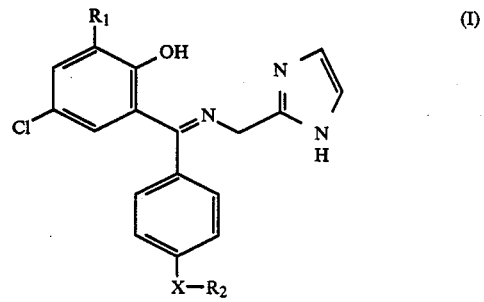

wherein
$R_1$ is chlorine or methyl,
X is a thio or sulphonyl group, and
$R_2$ is a $C_1$–$C_4$ alkyl, allyl, cyclohexyl or 2-pyridyl group, a phenyl group optionally substituted by methyl or one or two halogen atoms, or a benzyl group optionally substituted by a halogen atom, a methyl group or a methoxy group, or an addition salt with a pharmaceutically acceptable acid finds use in the treatment of ulcers.

4 Claims, No Drawings

N-(IMIDAZOLYLMETHYL)DIPHENYLAZOMETHINES AND COMPOSITIONS CONTAINING THEM

The present invention relates to N-(imidazolylmethyl)diphenylazomethines, their preparation and to the pharmaceutical compositions containing them.

The invention provides a compound which is an N-(imidazolylmethyl)diphenylazomethine derivative of general formula (I)

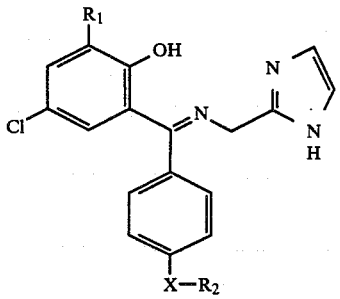

wherein
$R_1$ is chlorine or methyl,
X is a thio or sulphonyl group, and
$R_2$ is a a $C_1$–$C_4$ alkyl, allyl, cyclohexyl or 2-pyridyl group, a phenyl group optionally substituted by methyl or one or two halogen atoms, or a benzyl group optionally substituted by a halogen atom, a methyl group or a methoxy group, or an addition salt with a pharmaceutically acceptable acid.

Among the preferred compounds of the invention, there may be mentioned those of formula (I) in which is a sulphonyl group and $R_2$ is a benzyl group, especially when $R_1$ is chlorine, as well as those of formula (I) in which X is a thio group and $R_2$ is a 2-pyridyl group.

The compounds of the invention may be prepared by a process which comprises reacting a benzophenone of formula (II)

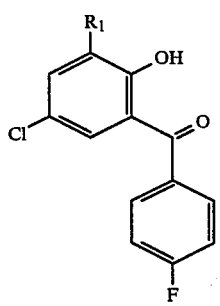

wherein $R_1$ is as defined above with the sodium salt of a mercaptan of formula $R_2$—SH, wherein $R_2$ is as defined above, in the heated state and in a solvent to produce an intermediate compound of formula (III)

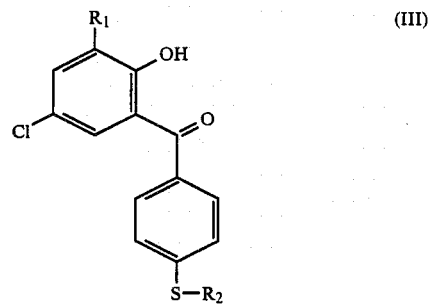

optionally oxidizing the intermediate compound of formula (III) to convert the thio group into a sulfonyl group, condensing the compound of formula (III) or its oxidation product of formula (IV)

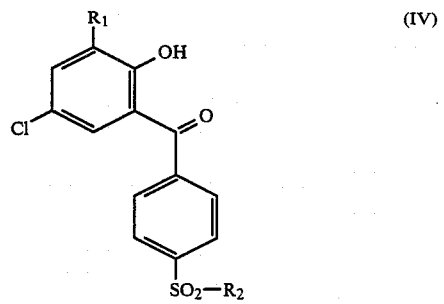

with (1H-imidazol-2-yl)methanamine in the heated state and in a solvent to produce an N-(imidazolylmethyl)diphenylazomethine derivative of formula (I), and if desired converting the derivative of formula (I) into an addition salt with a pharmaceutically acceptable acid. This process is illustrated by the reaction scheme set out below.

The reaction of the benzophenone of formula (II) with the sodium salt of a mercaptan of formula $R_2$—SH is preferably carried out using dimethyl sulphoxide as solvent. If a compound (I) is desired in which X denotes a sulphonyl group, the intermediate of formula (III) is oxidized, for example by means of 3-chloroperbenzoic acid. Ethanol is the preferred solvent when the compound of formula (III) or its oxidation product of formula (IV) is condensed with (1H-imidazol-2-yl)methanamine. The starting benzophenones (II) are known and may be prepared, for example, according to a process described in GB-A-2,111,051.

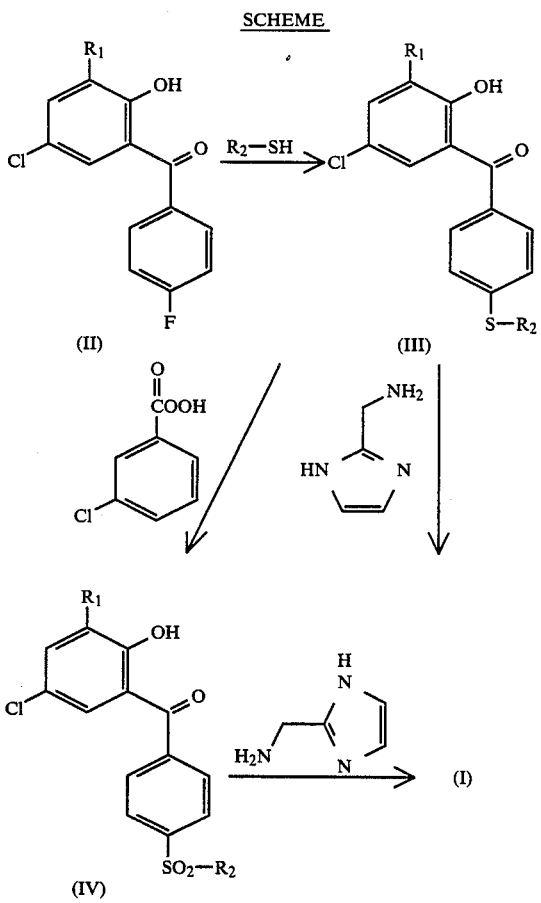

SCHEME

The Examples which follow illustrate in detail the preparation of the compound of the invention. The structures of the products obtained were confirmed by microanalyses and IR and NMR spectrum analysis.

EXAMPLE 1

2-[[4-(Benzylsulphonyl)phenyl]-{[(1H-imidazol-2-yl)methyl]imino}methyl]-4,6-dichlorophenol 1.1.

[4-(Benzylthio)phenyl]-(3,5-dichloro-2-hydroxyphenyl)methanone 5.2 g of sodium are placed in 250 ml of ethanol, 13.2 ml of thiobenzyl alcohol are added, the mixture is stirred for 30 minutes and the solvent is driven off.

The residue is dissolved with 200 ml of dimethyl sulphoxide, 32 g of (3,5-dichloro-2-hydroxyphenyl)-(4-fluorophenyl)methanone are added and the mixture is heated to 100° C. for 8 hours under argon.

The dimethyl sulphoxide is evaporated off, the residue taken up in dichloromethane and the solution washed with 10% strength hydrochloric acid. The organic phase is separated, dried over magnesium sulphate and eveporated.

The residue is purified by chromatography on silica, eluting with dichloromethane, and the purified fraction is recrystallized in cyclohexane.

Melting point: 102°-103° C.

1.2.

[4-(Benzylsulphonyl)phenyl]-(3,5-dichloro-2-hydroxyphenyl)methanone 22 g of the ketone prepared according to 1.1. are dissolved in 600 ml of dichloromethane, 24.4 g of 3-chloroperbenzoic acid are added and the mixture is stirred for 1 hour.

The mixture is then filtered, the precipitate being washed with dichloromethane, and the filtrate is evaporated almost to dryness.

The residue is purified by chromatography on silica, eluting with chloroform, and the purified fraction is recrystallized in ethanol.

Melting point: 153°-154° C.

1.3.

2-[[4-(Benzylsulphonyl)phenyl]-{[(1H-imidazol-2-yl)methyl]imino}methyl]-4,6-dichlorophenol 3.5 g of (1H-imidazol-2-yl)methanamine dihydrochloride and 3.5 g of sodium bicarbonate are introduced into 350 ml of ethanol, and the mixture is heated under reflux for 30 minutes. 6 g of the ketone prepared according to 1.2. are then added and the mixture is left heated for a further 3 hours under reflux.

The salts are separated by filtration, the ethanol is evaporated off, the residue is purified by chromatography on silica, eluting with a 95:5 dichloromethane/methanol mixture, and the purified fraction is recrystallized in ethanol.

Melting point: 197°-198° C.

EXAMPLE 2

2-[[4-(Ethylsulphonyl)phenyl]-{[(1H-imidazol-2-yl)methyl]imino}methyl]-4,6-dichlorophenol 2.1.

[4-(Ethylthio)phenyl]-(3,5-dichloro-2-hydroxyphenyl)methanone 1.30 g of sodium are placed in 200 ml of ethanol, 2 ml of ethanethiol are added, the mixture is stirred for 15 minutes and the solvent is driven off.

The residue is dissolved with 200 ml of dimethyl sulphoxide, 8 g of (3,5-dichloro-2-hydroxyphenyl)-(4-fluorophenyl)methanone are added and the mixture is heated to 100° C. for 8 hours under argon.

The dimethyl sulphoxide is evaporated off, the residue taken up in dichloromethane and the solution washed with 10% strength hydrochloric acid. The organic phase is separated, dried over magnesium sulphate and evaporated.

The residue is purified by chromatography on silica, eluting with a 40:60 dichloromethane/cyclohexane mixture, and the purified fraction is recrystallized in cyclohexane.

Melting point: 87°-89° C.

2.2.

[4-(Ethylsulphonyl)phenyl]-(3,5-dichloro-2-hydroxyphenyl)methanone 10 g of the ketone prepared according to 2.1. are dissolved in 250 ml of dichloromethane, 13 g of 3-chloroperbenzoic acid are added and the mixture is stirred for 1 hour.

The mixture is then filtered, the precipitate being washed with dichloromethane, and the filtrate is evaporated almost to dryness. The residue is purified by chromatography on silica, eluting with dichloromethane, and the purified fraction is recrystallized in ethanol.
Melting point: 120°-121° C.

2.3.
2-[[4-(Ethylsulphonyl)phenyl]-{[1H-imidazol-2-yl)methyl]imino}methyl]-4,6-dichlorophenol 3 g of (1H-imidazol-2-yl)methanamine and 3 g of sodium bicarbonate are introduced into 300 ml of ethanol, and the mixture is heated under reflux for 30 minutes. 5 g of the ketone prepared according to 2.2. are then added and the mixture is left heated for a further 3 hours under reflux.

The salts are separated by filtration, the ethanol is evaporated off, the residue is purified by chromatography on silica, eluting with a 98:2 dichloromethane/methanol mixture and the purified fraction is recrystallized in ethanol.
Melting point: 194°-195° C.

The table which follows illustrates the structures and physical properties of some compounds according to the invention.

TABLE (I)

| Compound | $R_1$ | X | $R_2$ | M.P. (°C.) |
|---|---|---|---|---|
| 1 | Cl | S | ethyl | 190–191 |
| 2 | Cl | S | n-propyl | 146–148 |
| 3 | Cl | S | i-propyl | 191–193 |
| 4 | Cl | S | allyl | 155–157 |
| 5 | Cl | S | cyclohexyl | 177–178 |
| 6 | Cl | S | 2-pyridinyl | 209–210 |
| 7 | Cl | S | phenyl | 199–201 |
| 8 | Cl | S | 4-methylphenyl | 194–196 |
| 9 | Cl | S | 4-chlorophenyl | 184–186 |
| 10 | Cl | S | 3,4-dichlorophenyl | 187–188 |
| 11 | Cl | S | benzyl | 175–176 |
| 12 | $CH_3$ | S | benzyl | 178–180 |
| 13 | Cl | S | 4-chlorobenzyl | 172–174 |
| 14 | Cl | S | 4-methoxybenzyl | 186–187 |
| 15 | Cl | $SO_2$ | ethyl | 194–195 |
| 16 | Cl | $SO_2$ | n-propyl | 195–196 |
| 17 | Cl | $SO_2$ | i-propyl | 192–193 |
| 18 | Cl | $SO_2$ | cyclohexyl | 222–224 |
| 19 | Cl | $SO_2$ | phenyl | 217–218 |
| 20 | Cl | $SO_2$ | 4-methylphenyl | 235–237 |
| 21 | Cl | $SO_2$ | benzyl | 197–198 |
| 22 | $CH_3$ | $SO_2$ | benzyl | 212–214 |
| 23 | Cl | $SO_2$ | 4-chlorobenzyl | 227–228 |
| 24 | Cl | $SO_2$ | 4-methoxybenzyl | 208–210 |

The compounds of the invention were tested in pharmacology. Their anti-ulcerative activity was shown in the stress ulcer and phenylbutazone-induced ulcer tests.

Stress ulcer

The technique used is that of Senay and Levine, Proc. Soc, Exp. Biol. 1967, 124, 1221–1223, Peptic Ulcers. Edited by C. J. PFEIFER. p. 92–97, on female Wistar rats weighing 180–210 g, fasted for the preceding 20 hours and divided into randomized groups.

The animals are restrained in cylindrical boxes 20 cm × 5 cm and placed in a cold room in which the temperature is maintained at 2°-4° C.

The test compounds are administered p.o. in the proportion of 10, 30 and 100 mg/kg immediately before the animals are placed in restraint, the control rats receiving only placebo.

2 hours later, the animals are sacrificed by inhalation of chloroform.

The stomachs are removed and the degree of ulceration is noted.

The compounds of the invention significantly decrease (up to 83% at the dose of 30 mg/kg) the stress ulcers.

Phenylbutazone-induced ulcer

The test is performed on female Wistar rats weighing 180–210 g, fasted for the preceding 20 hours and divided into randomized groups. The ulcers are induced by the oral administration of phenylbutazone dissolved mole for mole with sodium hydroxide, at a dose of 200 mg/kg.

The test compounds are administered p.o. in the proportion of 10, 30 and 100 mg/kg, 30 minutes before the ingestion of phenylbutazone, the control animals receiving only placebo.

Two hours after the administration of the ulcerogenic agent, the animals are sacrificed by inhalation of chloroform.

The stomachs are removed and the degree of ulceration is noted.

The compounds of the invention significantly decrease (up to 98% at the dose of 30 mg/kg) the phenylbutazone-induced ulcers.

The compounds of the invention can hence be used for treatment of gastric, duodenal or gastroduodenal ulcers.

They can be administered orally or parenterally, in the form of pharmaceutical compositions containing the active substance in association with any suitable excipient, for example in the form of tablets, dragees, capsules or gelatin capsules, or of solutions or suspensions for oral administration or for injection.

The daily dose can be from 10 to 2,000 mg of active substance in man.

We claim:

1. A compound which is selected from an N-(imidazolylmethyl diphenylazomethine derivative of the formula (I)

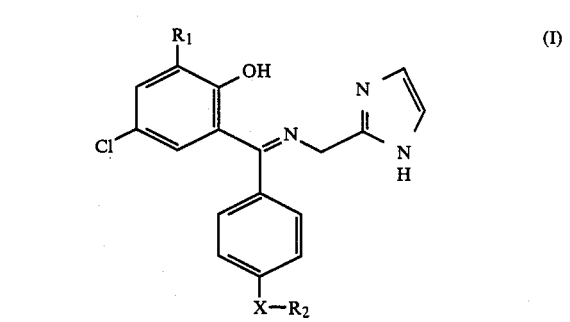

wherein
$R_1$ is selected from chlorine and methyl,
X is a group selected from thio and sulphonyl groups, and
$R_2$ is a group selected from 2-pyridyl group, a phenyl group unsubstituted or substituted by at least one substituent selected from a methyl, one halogen atom and two halogen atoms, and a benzyl group unsubstituted or substituted by a substituent selected from a halogen atom, a methyl group and a methoxy group, and an addition salt thereof with a pharmaceutically acceptable acid.

2. A compound according to claim 1, wherein X is a sulphonyl group and $R_2$ is a benzyl group.

3. A compound according to claim 1, wherein X is a thio group and $R_2$ is a 2-pyridyl group.

4. A pharmaceutical composition for the treatment of gastric, duodenal and gastroduodenal ulcers which comprises as active ingredient an effective anti-ulcer amount of a compound of claim 1 in association with a pharmaceutically acceptable exipient.

* * * * *